(12) United States Patent
Higgins

(10) Patent No.: US 6,840,116 B2
(45) Date of Patent: Jan. 11, 2005

(54) KELVIN SENSED HOT-WIRE ANEMOMETER

(75) Inventor: John Higgins, Santa Ana, CA (US)

(73) Assignee: SensorMedics Corporation, Yorba Linda, CA (US)

(*) Notice: Subject to any disclaimer, the term of this patent is extended or adjusted under 35 U.S.C. 154(b) by 37 days.

(21) Appl. No.: 10/230,517

(22) Filed: Aug. 29, 2002

(65) Prior Publication Data

US 2004/0040386 A1 Mar. 4, 2004

(51) Int. Cl.[7] .............................. G01P 5/06; G01F 1/68
(52) U.S. Cl. ............................. 73/861.85; 73/204.27; 128/200.24
(58) Field of Search .................... 73/204.11, 204.17, 73/204.23, 204.25, 204.27, 861.85; 128/200.24

(56) References Cited

U.S. PATENT DOCUMENTS

| 5,282,385 A | * | 2/1994 | Kayano et al. ......... 73/204.27 |
| 2002/0100474 A1 | * | 8/2002 | Kellner et al. ......... 128/200.24 |

OTHER PUBLICATIONS

Beta Evaluation of the Enhanced Mass Flow Sensor (emfs) and Vmax Spectra Software, by SensorMedics Corp. Jun. 14, 2001.*

Updat: Beta Evaluation of the Enhanced Mass Flow Sensor (emfs) and Vmax Spectra Software, by SensorMedics Corp. Oct. 1, 2001.*

"Tech Support: Applications Note 20: Quad Tracking Power Supply Manager," Summit Microelectronics, Inc.; printed from <http://www.summitmicor.com/tech_support/notes/note20.htm> on Mar. 30, 2002.

"Hot–Wire Anemometers: Introduction", efunda engineering fundamentals, printed from <http://www.efunda.com/designstandards/sensors/hot_wires/hot_wires_theory.cfm> on Mar. 31, 2002.

Hot–Wire Anemometers: Introduction, Overview, efunda engineering fundamentals, printed from http://www.efunda.com/designstandards/sensors/hot_wires/hot_wires_intro.cfm> on Mar. 21, 2002.

* cited by examiner

*Primary Examiner*—Harshad Patel
(74) *Attorney, Agent, or Firm*—Sidley Austin Brown & Wood LLP

(57) ABSTRACT

A Kelvin sensed hot-wire anemometer includes four electrically conductive pins and a filament welded to all four pins, preferably using a single filament. A current source is coupled to the two innermost pins so as to provide current flow in the segment of filament between the two innermost pins. The two outermost pins are coupled to a high impedance voltage sense amplifier that senses the voltage drop across the energized segment of filament between the two innermost pins. The resistance of the filament is determined based on the current provided to the filament and the measured voltage. The Kelvin sensed hot-wire anemometer can be used in a number of applications, including, but not limited to medical devices that measure gas flow rates during inhalation and exhalation.

17 Claims, 5 Drawing Sheets

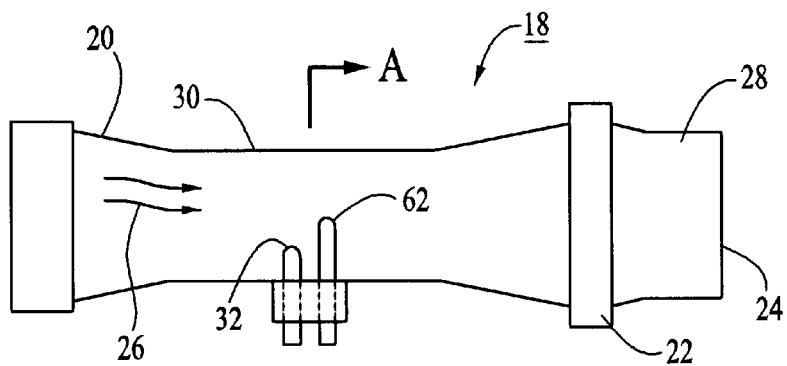
FIG. 4A
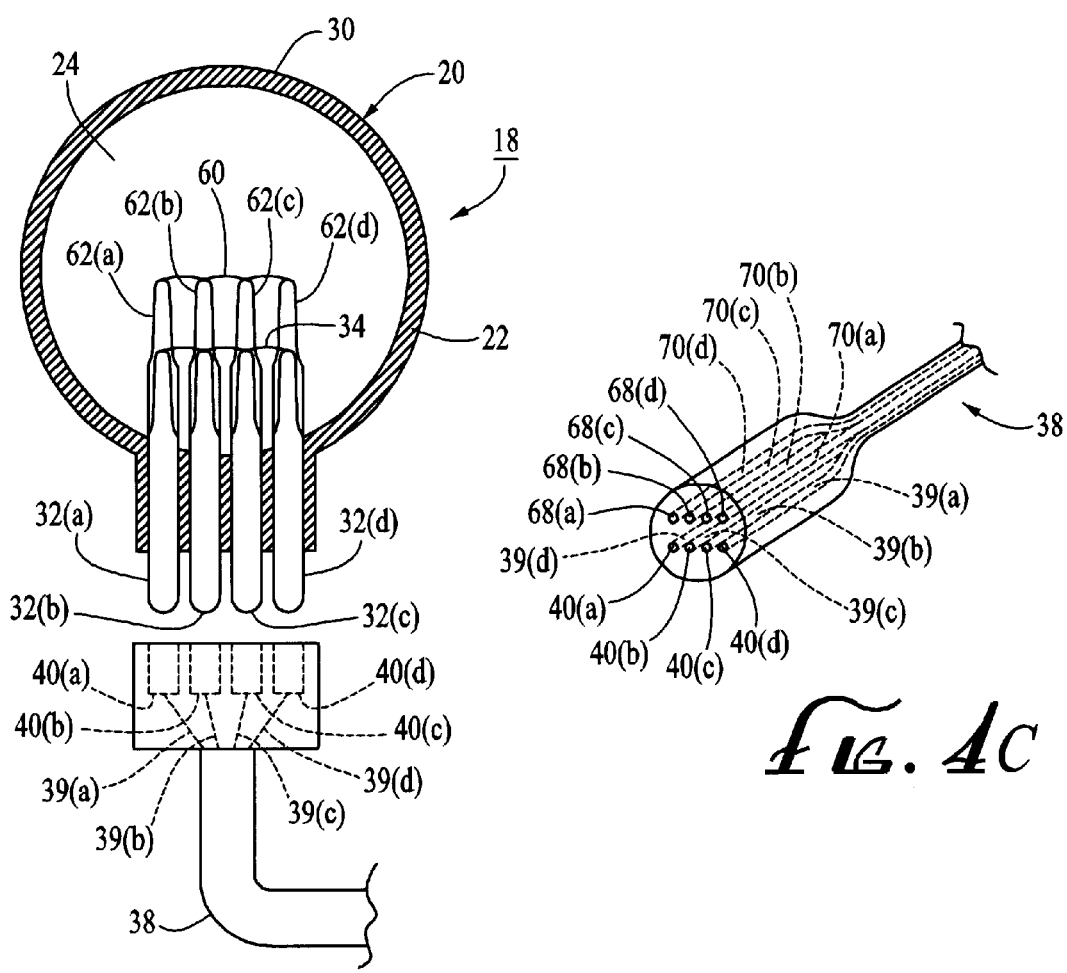
FIG. 4B
FIG. 4C

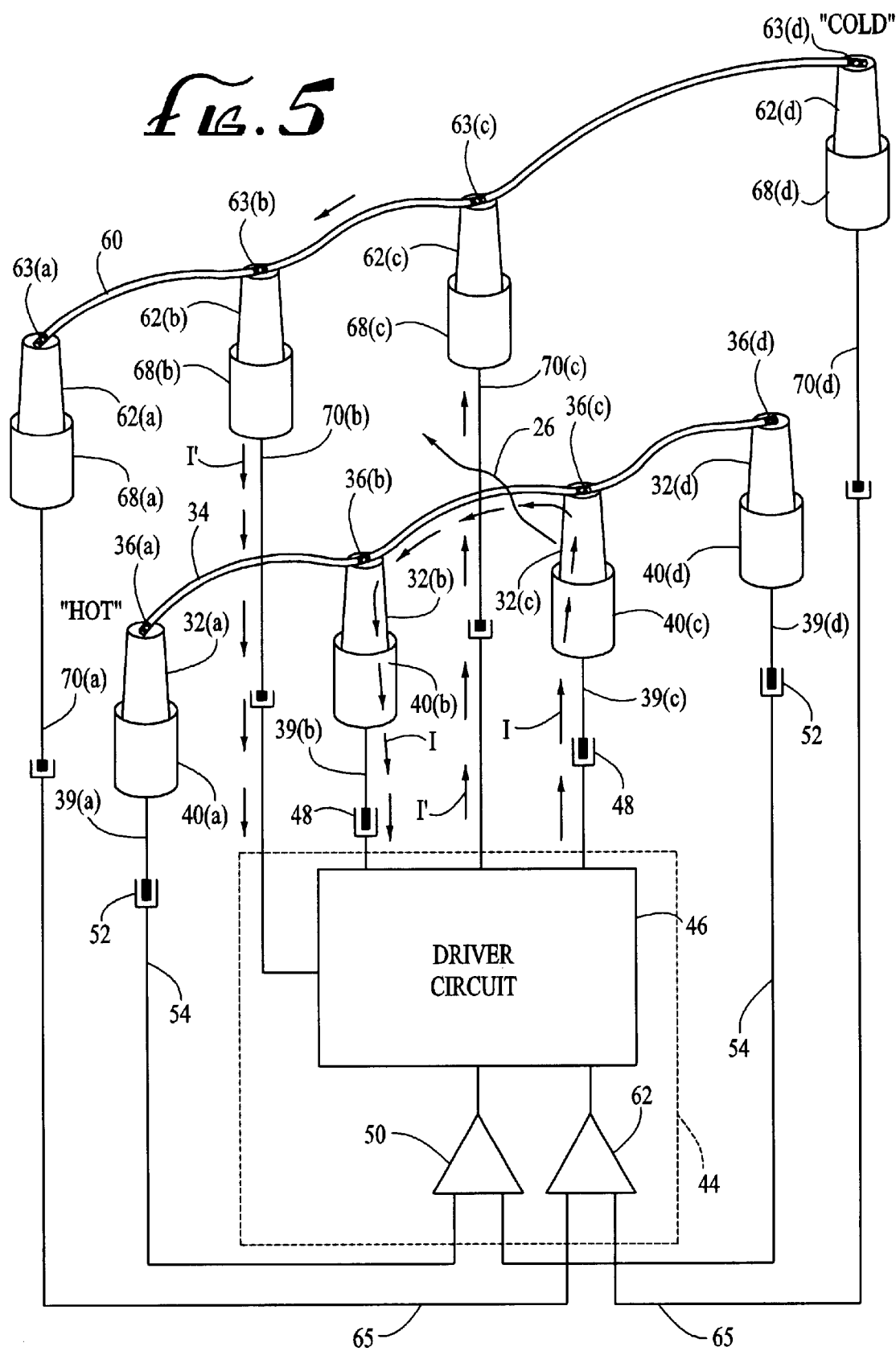

KELVIN SENSED HOT-WIRE ANEMOMETER

FIELD OF THE INVENTION

The field of the invention relates to hot-wire anemometers. Specifically, the invention relates to hot-wire anemometers for use in measuring the combined temperature and flow rate of a fluid.

BACKGROUND OF THE INVENTION

Hot-wire anemometers are most often used to measure fluid velocity based on the amount of heat connected away by a fluid passing over a heated wire. In typical hot-wire anemometers, a hot wire or filament is heated by either a constant current (constant-current anemometers) or, alternatively, heated to a constant temperature (constant-temperature anemometers). In either case, the amount of heat lost due to convection is a function of the fluid velocity passing over the filament.

The amount of heat that is dissipated by a heated filament located in a fluid stream depends on a number of factors including the filament's temperature, the geometry of the filament, the temperature of the fluid, and the fluid velocity. The filament's temperature is determined by measuring its electrical resistance. Empirical data and/or mathematical algorithms are used to calculate the temperature and the flow rate based on the measured resistance. Because metals used to fabricate suitable filaments have resistivity coefficients on the order of $0.1\%/°$ C., a high degree of accuracy is needed for measuring the actual resistance of the filament.

One medically-related application for hot-wire anemometers is their use in measuring the inspiration and expiration flow rates of a patient. Many lung function tests require knowing details on the rate at which air is entering and exiting a patient's lungs. Because the maximum realistic flow rate range encountered during inspiration and expiration is relatively low (e.g., between 0 and about 20 L/s), the resistance change in the filament is also small. For example, a filament having a resistance of 2.2 ohms at room temperature may only see a 0.03 ohm change in resistance over the entire realistic flow rate range. Because there is such a small change in the resistance in the filament, it is imperative that this change be measured with great accuracy and precision.

In prior art hot-wire anemometers, for example, as shown in FIGS. 1(*a*) and 1(*b*), a single wire anemometer probe 2 is used that is disposed inside a tubular housing. A filament 6 (shown in FIG. 1(*b*)) is welded between two pins 8 (one is obstructed from view in FIG. 1(*a*)) that extend from the middle of the probe 2 to outside the housing 4. The probe 2 is detachably attached to a cable 10 which has mating receptacles (not shown) for receiving the two pins 8. The cable 10 communicates with circuitry for calculation of the gas flow rate passing over the filament 6. There are several problems, however, with the prior art probe 2 that prevents the acquisition of accurate and precise resistance measurements.

In the prior art probe 2, there is no way to differentiate between resistivity of the filament 6 and resistivity caused by the cable 10 and the connection between the cable 10 and the two pins 8. Any resistance change caused by the cable 10 and/or the connection will be seen by the circuitry as a change in the resistance of the filament 6, thereby resulting in an erroneous temperature and gas flow calculation. There are several mechanisms by which resistance errors can be introduced in the prior art probe 2. These include, for example, (1) changes in ambient temperature, (2) time variations, and (3) physical disturbance/movement of the cable 10. Some of these errors cannot be eliminated nor reversed without a complete recalibration of the probe 2, which can take a considerable amount of time and effort.

Practical considerations require that the probe be designed in such a manner that allows a user to attach and remove the probe from a cable connecting the probe to the unit housing the electronics. This is particularly true when the probe is disposable or requires frequent replacement, maintenance, or cleaning. Consequently, cables and connectors are virtually required in all probe designs, thereby insuring the existence of the aforementioned error mechanisms.

Thus, there is a need for a detachable hot-wire anemometer probe that can precisely and accurately measure the resistance of a filament without the introduction of resistance errors caused by various environmental artifacts. The probe unit would be modular in that it could be attached/disconnected to a separate device containing the circuitry using a conventional cable.

SUMMARY OF THE INVENTION

In a first aspect of the invention, a hot-wire anemometer includes four electrically conductive pins comprising a pair of outer pins and a pair of inner pins. A filament is welded to each of the four electrically conductive pins, preferably using a single filament on all four pins. A current source is coupled to the pair of inner pins and adapted to provide current flow in the filament between the pair of inner pins. A voltage sense amplifier is coupled to the pair of outer pins.

In a second aspect of the invention, the hot-wire anemometer of the first aspect includes a second set of four electrically conductive pins including a pair of outer pins and a pair of inner pins. A second filament is welded to each of the four electrically conductive pins (second set). A current source is coupled to the second pair of inner pins and adapted to provide current flow in the second filament between the second pair of inner pins. A voltage sense amplifier is also provided and coupled to the second pair of outer pins.

In this second embodiment, one of the filaments (either the first or second) is used to measure the temperature of the fluid. The other filament is heated to a pre-determined temperature above the measured temperature of the fluid. The power supplied to the heated filament is then used to calculate the flow rate of the fluid across the filament.

It is thus an object of the invention to provide a hot-wire anemometer that precisely measures the actual or true resistance of the filament using a Kelvin sensing scheme.

It is a further object of the invention to provide a hot-wire anemometer that can be used to obtain real-time temperature and flow-rate measurements of a moving fluid. While the device has a preferred use in the medical field, the device and method of use is not so limited and can be used to measure fluid velocity and temperature in any number of settings. Similarly, while the device is primarily contemplated for use in measuring the flow rate and temperature of gases, the device and method can also be applied to liquids.

BRIEF DESCRIPTION OF THE DRAWINGS

FIG. 1(*b*) is an end view of the prior art probe of FIG. 1(*a*). FIG. 1(*b*) also shows a detachable cable.

FIG. 2(*b*) is an end view of the constricted region of the probe of FIG. 2(*a*) taken along the line A—A. Also shown is the cable and the unit housing the circuitry.

FIG. 4(a) is a side view of a probe according to another embodiment.

FIG. 4(b) is an end view of the constructed region of the probe of FIG. 4(a) taken along the line A—A. The detachable cable is also shown.

FIG. 4(c) is a perspective view of a terminal end of a cable.

FIG. 5 is a schematic view of a hot-wire anemometer with its associated circuitry according to the embodiment shown in FIGS. 4(a), 4(b), and 4(c).

DETAILED DESCRIPTION OF THE PREFERRED EMBODIMENTS

Figure 1A:
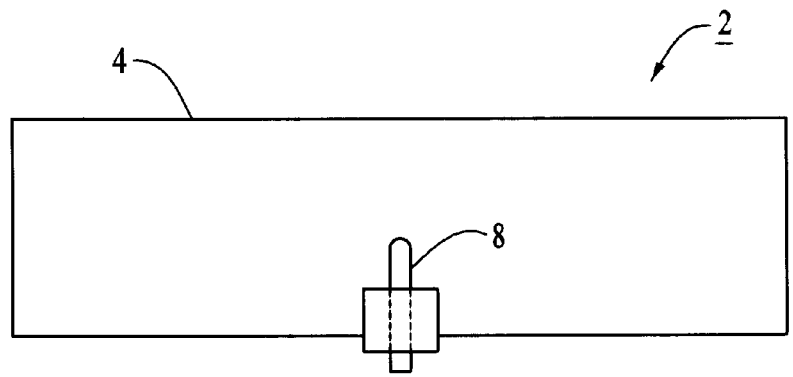
FIG. 1(*a*) is a side view of a prior art probe.
Figure 1B:
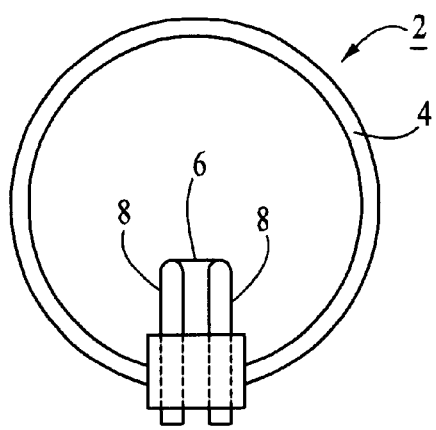
Figure 1B:
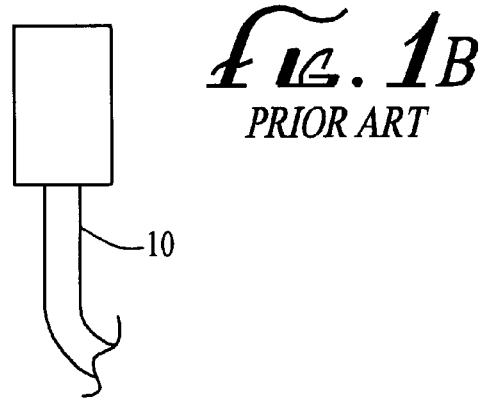
Figure 2A:
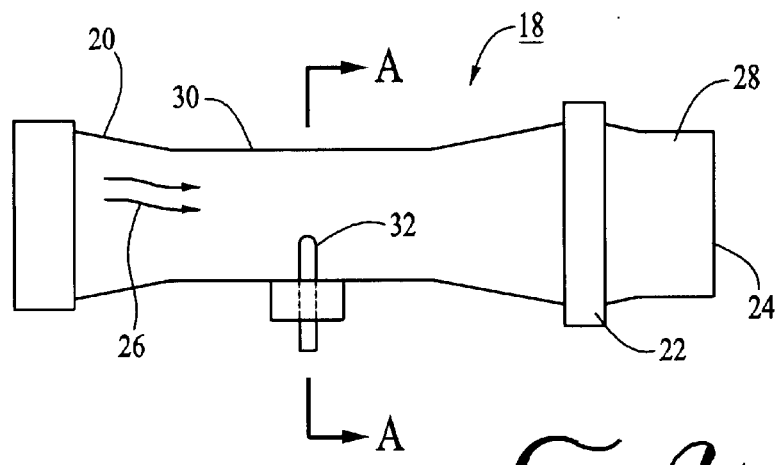
FIG. 2(*a*) is a side view of a probe according to one embodiment.
Figure 2B:
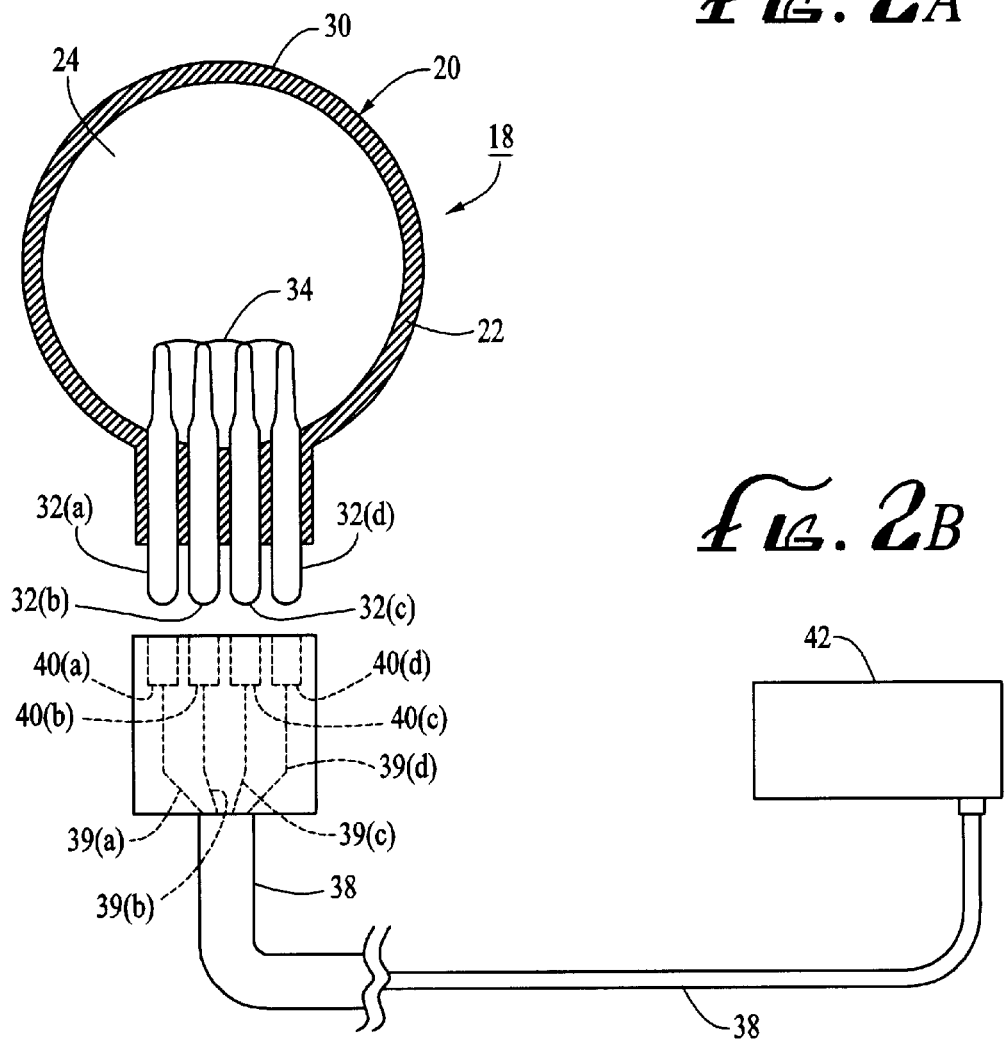

FIGS. 2(a) and 2(b) illustrate a hot-wire anemometer 18 according to a preferred embodiment of the invention. The hot-wire anemometer 18 is in the form of a probe 20 and includes a body 22 having a lumen 24 therethrough for the passage of a fluid 26. The fluid 26 may be a gas or a liquid depending on how the hot-wire anemometer 18 is used. For medical applications, including this preferred embodiment, the fluid 26 is a gas. The body 22 includes a mouthpiece section 28 over which a patient places his or her mouth. The body 22 also includes a constricted region 30 where gas measurements are preferably made. It should be understood, however, that gas measurements may be taken at other locations within the probe 20 that are outside the constricted region 30. The body 22 is preferably formed of a material such as plastic that can be cleaned using a liquid disinfectant.

Figure 3:
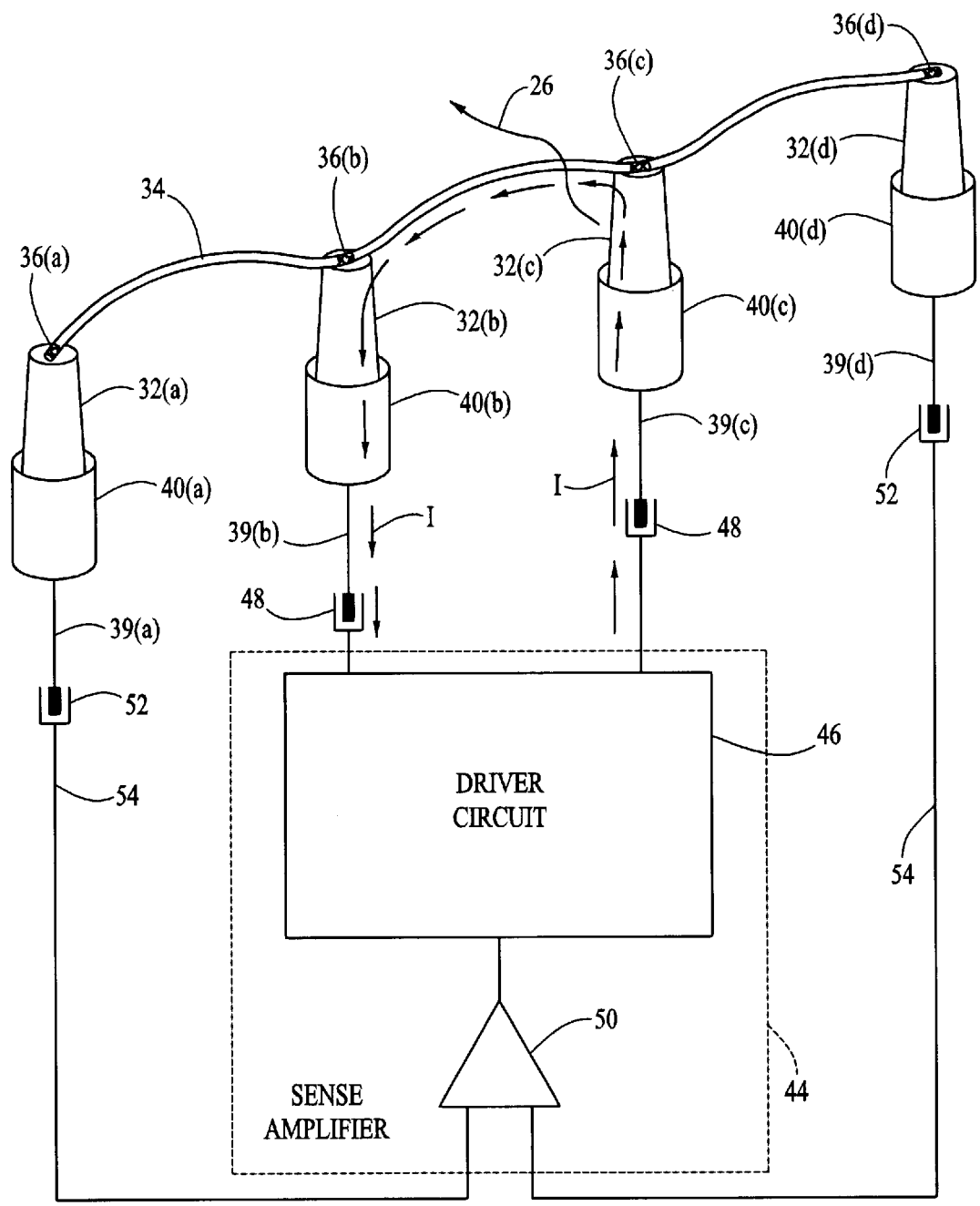
FIG. 3 is a schematic view of a hot-wire anemometer with its associated circuitry.

Referring now to FIG. 2(b), four pins 32(a–d) project through the body 22 and are held fixedly in place. The four pins include two outer pins (32(a) and 32(d)) and two inner pins (32(b) and 32(c)). The four pins 32(a–d) are preferably made of 304 stainless steel and plated with gold. One end of the pins 32(a–d) projects inside the body 22 into the lumen 24 while the opposing end of the pins 32(a–d) projects outside the body 22. A filament 34 is secured to the ends of the four pins 32(a–d) forming four nodes (two inner and two outer) at the connection point. Preferably, the filament 34 is secured to the pins 32(a–d) by spot welding. FIG. 3 shows the spot welds 36 on the top of each pin 32(a–d). The filament 34 is preferably made of 304 stainless steel. The filament 34 preferably has a circular cross-sectional profile with a diameter of approximately 0.001 inch.

A cable 38 is provided for engaging with the pins 32(a–d). The cable 38 preferably has mating receptacles 40(a–d) (shown in FIGS. 2(b) and 3) for engaging with the pins 32(a–d). The cable 38 allows the probe 20 to be attached and removed from the cable 38. The other end of the cable 38 is attached to a unit 42 housing the circuitry (disclosed in detail below) used to calculate the temperature and flow rate of the fluid 26 passing over the filament 34. The cable 38 includes a number of wires (a–d) corresponding to each receptacle 40(a–d). The cable 38 preferably allows the probe 20 to be used some distance away from the unit 42. For example, for many lung function tests, the patient is standing or engaging in some sort of physical activity (i.e., treadmill or bicycle). The cable 38 thus permits the probe 20 to be used in a variety of test conditions with the unit 42 located at a remote location that does not interfere with the particular lung function test.

FIG. 3 illustrates one preferred example of the circuitry 44 used in calculating the flow rate and/or temperature of a fluid 26 passing over a filament 34 of a hot-wire anemometer 18 according to a preferred embodiment of the invention. Also shown in FIG. 3 is a schematic representation of the pins 32(a–d), filament 34, and mating receptacles 40(a–d). In a preferred embodiment, the circuitry 44 includes a driver circuit 46 that provides current (shown by arrow I) to the hot-wire anemometer 18 so as to heat the filament 34. The driver circuit 46 is connected at connection points 48 to wires 39(b) and 39(c) of the cable 38. The wires 39(b) and 39(c) are, in turn, coupled to receptacles 40(b) and 40(c) of the cable 38. FIG. 3 shows the four pins 32(a–d) engaged with their respective receptacles 40(a–d). With respect to receptacles 40(b) and 40(c), current I is supplied by the driver circuit 46 through the receptacle 40(c) and through the corresponding pin 32(c) to the filament 34. The filament 34 is attached to the pins 32(a–d) through spot welds 36(a–d). Current I flows from pin 32(c) through the filament 34 toward pin 32(b). Current I returns to the driver circuit 46 via pin 32(b), the corresponding receptacle 40(b), and wire 39(b).

As seen in FIG. 3, current I passes only in the portion of filament 34 between the two inner pins 32(b) and 32(c). Current does not flow through outer pins 32(a) and 32(d) because these pins are coupled to a voltage measuring sense amplifier 50 that has a high input impedance. Consequently no current flows through pins 32(a) and 32(d). The two outer pins 32(a) and 32(d) are connected to the filament 34 via welds 36(a) and 36(d). The outer pins 32(a) and 32(d) engage with receptacles 40(a) and 40(d) that are electrically connected to wires 39(a) and 39(d), respectively. The wires 39(a) and 39(d) are coupled at connection points 52 to the inputs 54 to the voltage sense amplifier 50.

The voltage sense amplifier 50 detects the voltage drop across the segment of filament 34 between the two inner pins 32(b) and 32(c). Specifically, the voltage across welds 36(b) and 36(c) is identical to the voltage across the two inputs 54 to the voltage sense amplifier 50. Because no current can flow through the outer two filament segments (between pins 32(a)–32(b) and between pins 32(c) and 32(d)) as well as the pins 32(a), 32(d), receptacles 40(a), 40(d), and connection points 52, there is no voltage drop across these components. The voltage sense amplifier 50 thus receives the precise "true" voltage across the energized portion of the filament 34 (between pins 32(b) and 32(c)).

The voltage sense amplifier 50 amplifies the voltage to a level required by the circuitry 44 for determining the resistance of the energized portion of the filament 34. As shown in FIG. 3, in a preferred embodiment, the amplified voltage is supplied to the driver circuit 46. The resistance in the filament 34 is calculated using Ohm's law based on the current provided via the drive circuit 46 and the voltage seen by the voltage sense amplifier 50. In a preferred embodiment, the driver circuit 46 calculates the resistance based on the current and measured voltage drop. However, a separate circuit or microprocessor may be used to calculate the resistance of the filament 34.

FIG. 3 shows a fluid 26 passing over the filament 34. When the filament 34 is heated (above the temperature of the fluid 26) by application of an electrical current I and the filament 34 is exposed to fluid flow, convective heat transfer occurs from the filament 34 to the fluid 26. This heat transfer, being a function of the fluid velocity, causes small changes in the filament 34 temperature, and therefore its resistance. Because the hot-wire anemometer 18 precisely measures the resistance of the filament 34 (without resistance artifacts caused by cables, pins, receptacles, and welds), the temperature of the filament 34 can be obtained with great accuracy and precision. For any given fluid temperature and filament 34 geometry, the convective heat transfer value ($h_c$) can be determined from the filament 34 temperature change from its "zero fluid velocity" value. $h_c$ can then be directly correlated to fluid velocity using King's law. Advance knowledge of the fluid temperature is required in this embodiment.

FIGS. 4(a), 4(b), 4(c), and 5 show an alternative embodiment that uses two separate filament wires 34, 60. In this embodiment, the probe 20 is identical to that disclosed in the previous embodiment with the exception that hot-wire anemometer 18 includes a second set of four pins 62(a–d) and a second filament 60 welded via spot welds 63(a–d) to the second set of pins 62(a–d). Four nodes (two outer and two inner) are created at the locations where the pins 62(a–d) contact the filament 60. In this embodiment, the first set of pins 32(a–d) and the second set of pins 62(a–d) are used for different purposes. The first set of pins 32(a–d) is used just as the embodiment described above, namely, current I passes from a driver circuit 46 through pin 32(c) and to the region of the filament 34 located between the two inner pins 32(b) and 32(c). This current I heats the filament 34 as in the previously described embodiment. Current I returns to the driver circuit 46 via pin 32(b). The voltage drop on the filament 34 is measured using a voltage sense amplifier 50 connected to the two outer pins 32(a) and 32(d). In this regard, the first set of pins 32(a–d) and filament 34 are called "hot".

The second set of pins 62(a–d) and filament 60 are referred to as "cold". The second set of pins 62(a–d) and filament 60 are used to measure the temperature of the fluid 26 (i.e., gas) passing through the probe 20. The temperature of the fluid 26 is determined using the same Kelvin sensing techniques as the hot filament 34. In this regard, the temperature of the fluid 26 is determined from the temperature of the filament 60 which is obtained by its measured resistance. The filament 60 is preferably made of 304 stainless steel. The filament 60 preferably has a circular cross-sectional profile with a diameter of approximately 0.001 inch. In a preferred embodiment, filament 60 should match filament 34 in geometry and scale in order to match their thermal behavior.

In the cold filament 60, a very small current I' is passed through the filament 60 so as not to cause significant heating of the filament 60. The current I' is passed through the segment of filament 60 located between the two inner pins 62(b) and 62(c). The voltage drop on the filament 60 is measured with a separate voltage sense amplifier 62 via inputs 65. Preferably, the same driver circuit 46 receives the amplified voltage from the voltage sense amplifier 62. As with the hot wire, the resistance in the cold filament 60 is calculated based on the current I' and measured voltage using Ohm's law.

In this second embodiment, instead of the cable 38 having just four receptacles 40(a–d) and four wires 39(a–d), the cable 38 has a total of eight receptacles 40(a–d), 68(a–d) and eight wires 39(a–d), 70(a–d). FIG. 4(c) shows the full compliment of receptacles 40(a–d), 68(a–d) and wires 39(a–d), 70(a–d).

In the embodiment with the two filaments 34 and 60, the cold filament 60 is used to measure the temperature of the fluid 26. Preferably, the hot filament 34 is heated with a current I so as to maintain a constant temperature differential above the temperature of the fluid 26 measured by the cold filament 60. The second filament 34 is used to measure the flow rate of the fluid 26 based on its power consumption, which is a direct function of $h_c$. For example, the cold filament 60 might measure a gas temperature of 25° C. during patient inhalation. Consequently, the driver circuit 46 for the hot filament 34 would deliver a current I so as to heat the filament 34 to a predetermined temperature above the temperature of the gas. In the current example, the temperature differential might be set to 85° C. Accordingly, the hot filament 34 would be heated to a temperature of 110° C. While a 85° C. temperature differential has been disclosed, it should be understood that other temperature differentials may also be used. It is preferable that this embodiment is dynamic in that when the temperature of the fluid 26 changes the temperature of the filament 34 changes in a corresponding manner. The changes in the current I applied to the filament 34 can be done on a real-time or rear real-time basis. This embodiment is particularly advantageous because it cancels out the impact of temperature changes in the measured fluid 26 and surrounding environment.

In the preferred embodiments, the hot-wire anemometer 18 is used in conjunction with a probe 20 to measure the temperature and flow rate of a gas. It should be understood, however, that the hot-wire anemometer 18 may function without a body 22 and may just comprise four pins 32(a–d) and an electrically coupled filament 34. Similarly, while the hot-wire anemometer 18 is used to measure the temperature and flow rate of gases, the hot-wire anemometer 18 can be used in other applications where the fluid may be a liquid.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A hot-wire anemometer comprising:
   four electrically conductive pins comprising a pair of outer pins and a pair of inner pins;
   a filament welded to each of the four electrically conductive pins;
   a current source coupled to the pair of inner pins and adapted to provide current flow in the filament between the pair of inner pins; and
   a voltage sense amplifier coupled to the pair of outer pins.

2. The hot-wire anemometer according to claim 1, further comprising a body containing the four electrically conductive pins and the filament.

3. The hot-wire anemometer according to claim 2 wherein the current source and sense amplifier are coupled to the conductive pins using a detachable cable.

4. The hot-wire anemometer according to claim 2, wherein the four electrically conductive pins and the filament are located within a restricted region of the body.

5. The hot-wire anemometer according to claim 1, further comprising means for calculating the resistance of the filament between the pair of inner pins based on the current level of the current source and the voltage level detected by the sense amplifier.

6. The hot-wire anemometer according to claim 5, wherein the means calculates the temperature of a fluid passing over the filament.

7. The hot-wire anemometer according to claim 6, wherein the temperature is calculated on a real-time basis.

8. The hot-wire anemometer according to claim 6, wherein the fluid is a liquid.

9. The hot-wire anemometer according to claim 6, wherein the fluid is a gas.

10. The hot-wire anemometer according to claim 5, wherein the means calculates the flow rate of a fluid passing over the filament.

11. The hot-wire anemometer according to claim 7, wherein the flow rate is calculated on a real-time basis.

12. The hot-wire anemometer according to claim 10, wherein the fluid is a liquid.

13. The hot-wire anemometer according to claim 10, wherein the fluid is a gas.

14. The hot-wire anemometer according to claim 1, further comprising:
   a second set of four electrically conductive pins including a pair of outer pins and a pair of inner pins,
   a filament welded to each of the four electrically conductive pins;
   a current source coupled to the second pair of inner pins and adapted to provide current flow in the filament between the second pair of inner pins; and
   a voltage sense amplifier coupled to the second pair of outer pins.

15. The hot-wire anemometer according to claim 1, wherein the filament is a single filament welded to each of the four electrically conductive pins.

16. A method of measuring the temperature of a fluid comprising the steps of:
   providing a filament in the path of a moving fluid, the filament having four separate nodes along the length thereof;
   providing a current flow between the two inner nodes on the filament;
   measuring a voltage at the two outer nodes on the filament;
   determining the resistance of the filament between the two inner nodes based on the current flow and the measured voltage; and
   calculating the temperature of the fluid based on the resistance of the filament.

17. A method of measuring the flow rate of a fluid comprising the steps of:
   providing a filament in the path of a moving fluid, the filament having four separate nodes along the length thereof;
   providing a current flow between the two inner nodes on the filament;
   measuring a voltage at the two outer nodes on the filament;
   determining the resistance of the filament between the two inner nodes based on the current flow and the measured voltage; and
   calculating the flow rate of the fluid based on the resistance of the filament.

* * * * *